United States Patent [19]

Kojima et al.

[11] Patent Number: 5,116,706
[45] Date of Patent: May 26, 1992

[54] 1,2,4,5-BENZOYLENEBIS(NAPHTHO[1,8-DE]PYRIMIDINE) COMPOUNDS AND THEIR USE IN PHOTOSENSITIVE LAYERS

[75] Inventors: Yoshimi Kojima, Nara; Satoshi Katayama, Tenri; Yoshihide Shimoda, Nara; Hiroshi Sugimura, Osaka; Eiji Imada, Nara, all of Japan

[73] Assignee: Sharp Kabushiki Kaisha, Osaka, Japan

[21] Appl. No.: 605,160

[22] Filed: Oct. 31, 1990

Related U.S. Application Data

[62] Division of Ser. No. 369,849, Jun. 22, 1989, abandoned.

[30] Foreign Application Priority Data

Jun. 25, 1988 [JP] Japan .................. 63-157246

[51] Int. Cl.$^5$ .................................. G03G 5/04
[52] U.S. Cl. .................................. 430/58; 430/78
[58] Field of Search .................. 430/28, 58

[56] References Cited

U.S. PATENT DOCUMENTS

| | | | |
|---|---|---|---|
| 1,081,602 | 12/1913 | Flachslaender et al. | 544/245 |
| 3,342,818 | 9/1967 | Schefczik | 544/245 |
| 3,833,583 | 9/1974 | Kalz et al. | 544/245 |

FOREIGN PATENT DOCUMENTS

| | | | |
|---|---|---|---|
| 0349219 | 1/1990 | European Pat. Off. | 544/245 |
| 2236555 | 2/1974 | Fed. Rep. of Germany | 544/245 |

OTHER PUBLICATIONS

Dassigny, Chemical Abstracts, vol. 53: 8643h-8644g (1959).
Robin, Chemical Abstracts, vol. 53: 15583g-15584e (1959).
Manukian, Chemical Abstracts, vol. 64: 17602f-17603b (1966).
Maehara, Chemical Abstracts, vol. 78: 137954u (1973).
Kaempgen, Chemical Abstracts, vol. 79: 6783k (1973).
Wanatabe et al., Chemical Abstracts, vol. 88: 8499g (1978).

Primary Examiner—Marion E. McCamish
Assistant Examiner—S. Rosasco
Attorney, Agent, or Firm—Birch, Stewart, Kolasch & Birch

[57] ABSTRACT

1,2,4,5-Benzoylenebis(naphto[1,8-de]pyrimidine) compounds of the followig formula (I) or (II):

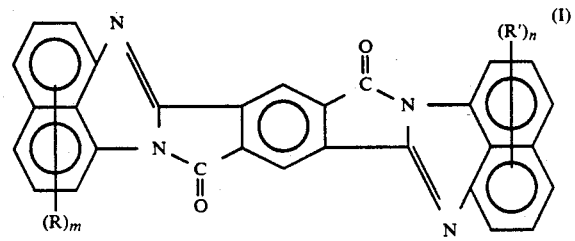

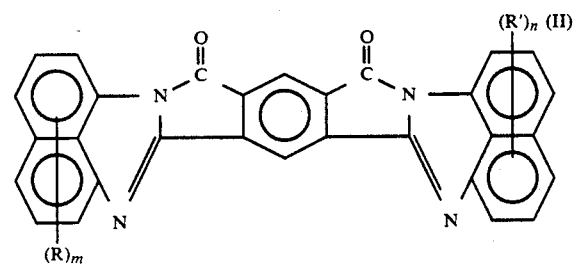

wherein R and R' are, the same or different, hydrogen atom, a halogen atom, hydroxyl group, nitro group, cyano group, an alkyl group which may be substituted, an alkoxyl group which may be substituted, an aryl group which may be substituted, an aralkyl group which may be substituted, a carboxyl group which may be esterified or a carbamoyl group which may be substituted and m and n each are an integer from 1 to 6, and photosensitive members for electrophotography having a photosensitive layer containing them.

13 Claims, 3 Drawing Sheets

1,2,4,5-BENZOYLENEBIS(NAPHTHO[1,8-DE]-PYRIMIDINE) COMPOUNDS AND THEIR USE IN PHOTOSENSITIVE LAYERS

This application is a divisional of application Ser. No. 07/369,849 filed on June 22, 1989 which is now abandoned.

BACKGROUND OF THE INVENTION

1. Field of the Invention

The present invention relates to novel pyrimidine compounds and their use. More particularly, it relates to novel 1,2,4,5-benzoylenebis (naphtho[1,8-de]-pyrimidine) compounds, which are organic photoconductive substances, and photosensitive members using them.

2. Description of the Prior Art

Generally, an electrophotography using a photoconductive photosensitive member is one of information recording means utilizing photoconductive phenomena.

In the electrophotography, the surface of the photosensitive member is uniformly charged by a corona discharge or the like, in darkness and then, by subjecting the charged surface to image exposure, the electric charge of the exposed portion is discharged selectively to form an electrostatic latent image at the unexposed portion of the surface. Next, the latent image is converted to a visual image by allowing charged colored fine particles (toner) to adhere to the latent image by means of electrostatic attraction force, etc., whereby an image is formed. The basic properties required for photoconductive photosensitive members used in the electrophotography techniques of these serial processes are:

(1) that the photosensitive members can be electrified in darkness at a suitable electric potential uniformly, (2) that they have a high, electric charge-retentivity in darkness and discharge of the electric charge from them is minor, (3) that they are superior in photosensitivity and quickly discharge the electric charge by photoirradiation, and the like. Moreover, it is required for the photoconductive photosensitive members to have good stability and endurance; such as, that the surface of them can be discharged easily, with a minor residual electric potential on the surface, that they have mechanical strength and are superior in flexibility, that their electric properties, especially, electrification property, remaining electric potential, etc., do not fluctuate even when they are used repeatedly, that they are resistant to heat, light, temperature, humidity, ozone deterioration, etc., and the like.

Photosensitive members for electrophotography now used practically may be divided broadly into two groups, one utilizing materials of inorganic series and one utilizing materials of organic series.

As representative photosensitive members of inorganic series, there can be mentioned those of selenium series, such as amorphous selenium (a-Se), amorphous arsenic selenide (a-$As_2Se_3$), etc., those comprising color-sensitized zinc oxide (ZnO) or cadmium sulfide (CdS) dispersed Zin a bonding resin, those using amorphous silicon (a-Si), and the like. As representative photosensitive members of organic series, there are those using a charge-transfer complex of 2,4,7-trinitro-9-fluorenone (TNF) and poly-N-vinylcarbazole (PVK), and the like.

These photosensitive members have many merits, but at the same time some demerits. For instance, photosensitive members of selenium series and photosensitive members using CdS have some questions in respect of their heat-resistance and can-stability. Moreover, there is a restriction in the use of those photosensitive members that, because of their toxicity, they cannot be simply thrown away but have to be recovered. Photosensitive members comprising ZnO dispersed in resin are now practically not used, because of their low sensitivity and inferior endurance. Amorphous silicon photosensitive members having merits, such as high sensitivity, high endurance, etc., have also problems that their manufacturing cost is high because of their complicated manufacturing process, that they give faulty images resulting from the fault of membrane which is inherent in amorphous silicon, and the like. Further, they have defects that their flexibility is not a satisfactory one, that their processing into various forms such as drum, sheet, etc., is not easy, and the like.

On the other hand, an attention is given for organic photosensitive members as the most important ones, because suitable organic materials without the problems on canstability and toxicity can be selected from existing various materials or organic materials having improved durability and low cost become available. However, there remains another disadvantage on sensitivity of organic photosensitive materials to be improved. The above described PVK-TNF charge-transfer complex series resulted from such improvement, but did not attain sufficient sensitivity. In addition, various sensitizing methods have been proposed. At present, the main current of organic photosensitive members practically used is occupied by laminate type photosensitive members (hereinafter, called "multilayer type photosensitive members") having a superior sensitizing property, which comprise a layer (hereinafter, called "charge-generating layer") containing a substance which allows generation of charge-carriers by photoirradiation (hereinafter, called "charge-generating substance") and a layer (hereinafter, called "charge-transporting layer") consisting mainly of a substance which accepts and transports the charge carriers generating in the charge-generating layer (hereinafter, called "charge-transporting substance").

As organic materials which may be used for the charge-generating layer of the above-mentioned multilayer type photosensitive members, bis-azo pigments such as chlorodianblue, etc., polycyclic quinone series pigments such as dibromoanthanthrone, etc., perillene, quinacridone or phthalocyanine series compounds, azulenium salt compounds, and the like, are known. However, some of these charge-generating materials are lacking in photoconductivity though they have a good absorption spectral property for photosensitive members, in the visual ray region, and some of them have an absorption spectral property not suitable for photosensitive members though they have a good photoconductivity. Thus, it was very difficult to compose a photosensitive member having a good sensitivity, by striving for coexistence of the absorption spectral property and the photoconductivity. The multilayer type photosensitive members provided with such charge-generating ① those wherein a thin layer formed by application of an organic amine solution of chlorodianblue is used as the charge-generating layer and a hydrazone compound is used as the charge-transporting substance of the charge-transporting transporting layer (Japanese Patent Publication No. SHO 55-42380 is referred to), ② those wherein a bis-azo compound is used as the charge-generating substance of the charge-generating layer and a hydrazone compound is used as the charge-transporting layer (Japanese Patent Application Laid-open No. SHO 59-214035 is referred to), ③ those wherein an azulenium salt compound is used as the charge-generating substance of the charge-generating layer and a hydrazone compound or the like is used as the charge-transporting layer (Japanese Patent Application Laid-open No. SHO 59-53850 is referred to), ④ those wherein a perillene derivative is used as the charge-generating substance of the charge-generating layer and an oxadiazole derivative is used as the charge-transporting layer (U.S. Pat. No. 3,871,882 is referred to), and the like.

However, these photosensitive members ①-④ were still insufficient in sensitivity, as they were used practically. Moreover, these hitherto known multilayer type photosensitive members had a problem in their stability they were used repeatedly.

Therefore, notwithstanding the above-mentioned many merits of the organic photoconductive substances, compared with inorganic ones, they were not so much used for photosensitive members for electrophotography because photosensitive members using them were inferior in sensitivity and endurance.

The present invention has been made in view of the above-described circumstances and its purpose resides in providing novel organic photoconductive substances and their use as photosensitive members for electrophotography having a high sensitivity.

As a result of keen investigations for photoconductive substances having a high sensitivity, which have been performed from the above-described view-points, the inventors of the present invention have found that a specific group of novel pyrimidine compounds are suitable as photoconductive substances. Thus, the present invention has been completed.

SUMMARY OF THE INVENTION

The present invention provides 1,2,4,5-benzoylenebis(naphtho[1,8-de]pyrimidine) compounds represented by the following formula (I) or (II):

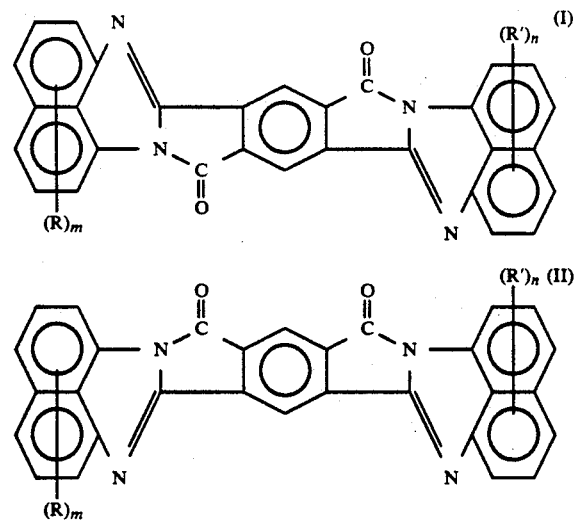

wherein R and R' each are hydrogen atom, a halogen atom, hydroxyl group, nitro group, cyano group, an alkyl group which may be substituted, an alkoxy group which may be substituted, an aryl group which may be substituted, an aralkyl group which may be substituted, an aralkyl group which may be substituted, a carboxyl group which may be esterified, a carbamoyl group which may be substituted, independently, R and R' may be identical with or different from each other and m and n each are an integer from 1 to 6, and photosensitive members having a photosensitive layer containing them.

The photosensitive members using the pyrimidine compounds of the present invention have a extremely high sensitivity and are superior in photoconductivity, compared with the conventional photosensitive members.

The photosensitive members containing the pyrimidine compounds of the present invention can be used not only in the field applying electrophotography, such as laser but also widely for a solar battery, a photosensor, etc.

DESCRIPTION OF THE PREFERRED EMBODIMENTS

Figure 1:
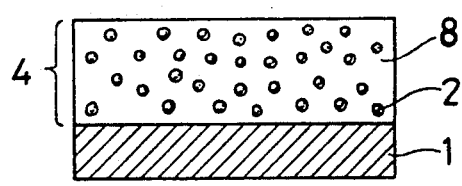
FIG. 1-8 are each an enlarged sectional diagram showing an Example of the photosensitive members of the present invention.

The 1,2,4,5-benzoylenebis(naphtho[1,8-de]pyrimidine) compounds of the present invention (hereinafter, called represented by the above-described general formula (I) or (II).

In the general formulae (I) and (II), R and R' each are hydrogen atom, a halogen atom, hydroxyl group, nitro group, cyano group, an alkyl group which may be substituted, an alkoxy group which may be substituted, an aryl group which may be substituted, and aralkyl group which may be substituted, a carboxyl group or a carbamoyl group which may be substituted, the R and R' may be identical with or different form each other, and m and n each are an integer from 1 to 6.

Examples of the halogen atoms are fluorine atom, chlorine atom, bromine atom and iodine atom.

The alkyl group includes straight or branched chain lower alkyl groups having from one to five carbon atoms, such as methyl group, ethyl group, n-propyl group, isopropyl group, etc. The alkyl group may be substituted by one or more substituents, such as a halogen atom, hydroxy group, nitro group, cyano group, etc. Chlorine atom or nitro group is preferable as the substituent.

The alkoxy group includes straight or branched chain lower alkoxy groups having from one to five carbon atoms, such as methoxy group, ethoxy group, n-propoxy group, isopropoxy group, etc. The alkoxy group may be substituted by one or more substituents, which are the same as those described for the above alkyl group. Chlorine atom or nitro group is preferable as the substituent.

The aryl group includes phenyl group, naphthyl group, etc. The aryl group may be substituted by one or more substituents, such as a halogen atom, nitro group, cyano group, hydroxy group, a lower alkyl group, a lower alkoxy group, a di-lower alkylamino group. The lower alkyl groups in the above substituents are straight or branched chain lower alkyl groups having from one to five carbon atoms.

The aralkyl group includes benzyl group, phenethyl group, etc. The aryl moiety thereof may be substituted by one or more substituents, which are the same as those described for the aryl group.

The carboxyl group may be in the form of an ester or salt group. The former is a lower alkyl-, an aryl ester group or the like. The latter is a sodium-, potassium salt group or the like. Examples of the ester group are methoxy carbonyl-, phenoxy carbonyl-, substituted phenoxy carbonyl group, etc.

Examples of the substituents for the carbamoyl group are an alkyl group, an alkoxy group, an aryl group, a hetero-aromatic group, etc. The alkyl group and the alkoxy group are the same as those described above. The aryl group includes phenyl group, naphthyl group, anthoranyl group, etc. It may be also substituted by one or more substituents, dibenzofuranyl group, etc. The carbamoyl group may be by two or more of these substituents.

In the pyrimidine compounds of the present invention, m and n each are preferably an integer of 6 when the R and R' each are a hydrogen atom, an integer of 1 or 2 when the R and R' each are a halogen atom, and an integer of 1 when the R and R' each are not a hydrogen atom or a halogen atom, respectively.

The pyrimidine compounds of the present invention may be prepared by utilizing of publicly known processes. For example, they may be prepared by treating pyromellitic anhydride of the following formula (III) with an aromatic diamine of the following general formulae (IV) and (V) (wherein, R, R', m and n have the same meaning as defined in the formulae (I) and (II)) in an inert solvent, at an elevated temperature, preferably at 100°-350° C., particularly temperature higher than 200° C. The reaction is performed until its completion. A reaction time of 3-24 hours is usually preferred (Bull. Chem. Soc. Japan, 25, 411-413 (1952); ibid. 27, 602-605 (1954) are referred to).

Examples of an inert solvents are nitrobenzene, an aprotic polar solvent, such as N-methylpyrrolidone, N,N-dimethylformamaide, N,N-dimethylacetamide, etc., a basic such as quinoline, etc., or a chlorine-series solvent, such as o-dichlorobenzene, etc., or in a mixture of these solvent.

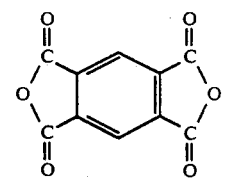

(III)

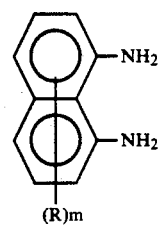

(IV)

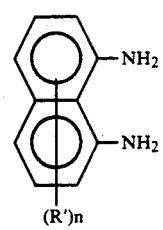

(V)

According to the above method, pyrimidine compounds represented by the above general formula (I) (trans- type) or formula (II) (cis- type) are obtained in the form of mixture. The pyrimidine compounds of the present invention include the isomers of trans-type and cis-type and the mixture thereof. It is able to separate the isomers by the conventional method, if necessary. The mixture, however, is sufficient to use as a photoconductive material.

Examples of pyrimidine compounds of the present invention are shown in the following, but do not limit the present invention. It is noted that only the trans-type compounds are given.

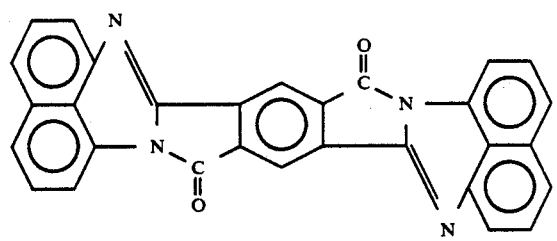

(1)

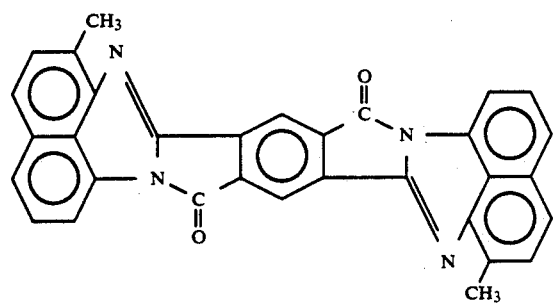

(2)

-continued
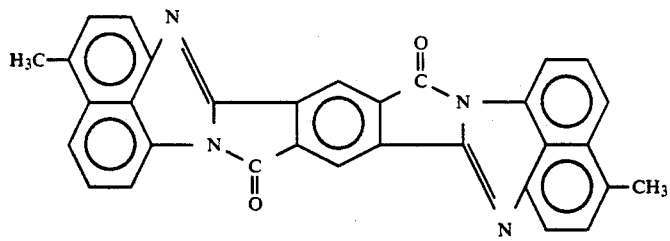
(3)
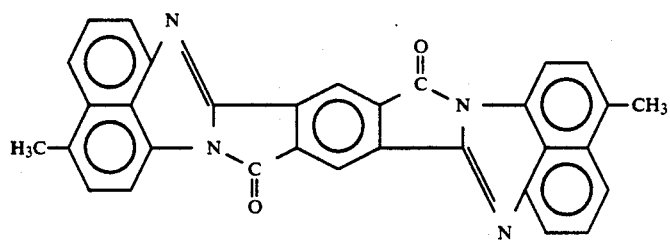
(4)
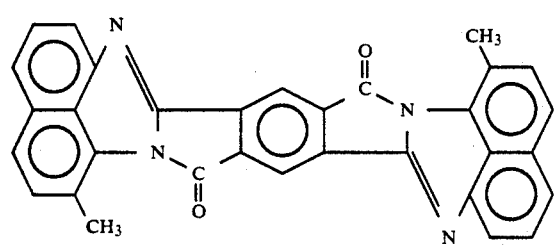
(5)
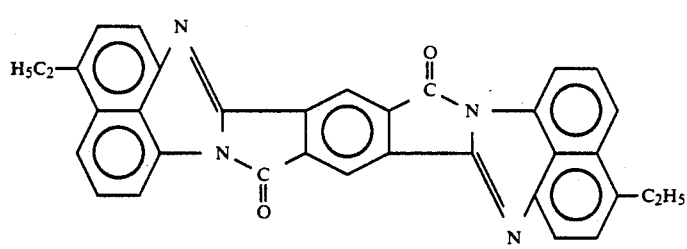
(6)
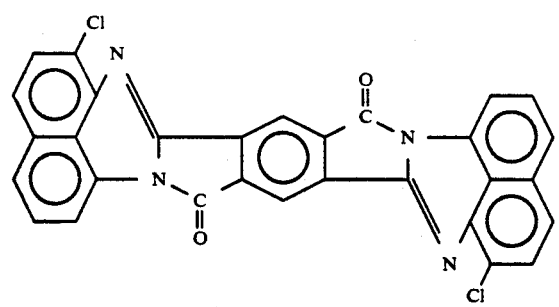
(7)
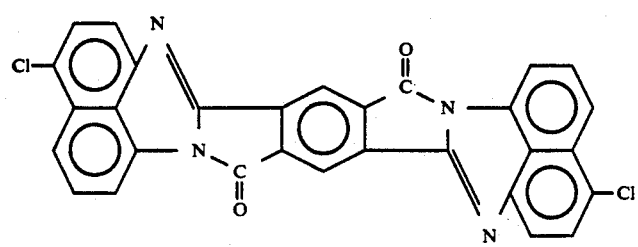
(8)

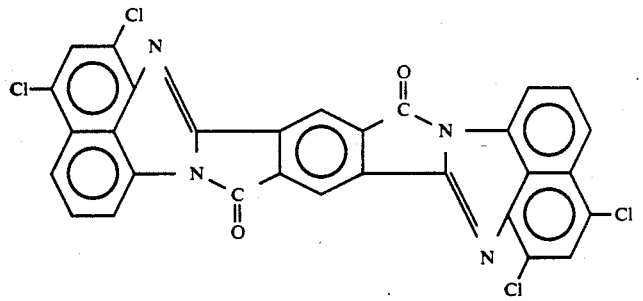
(9)
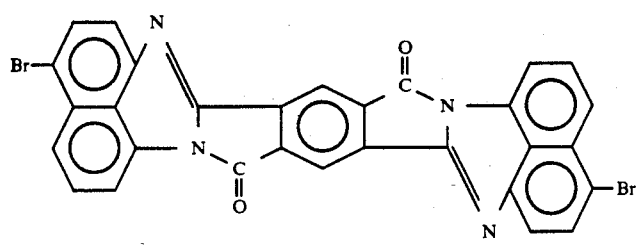
(10)
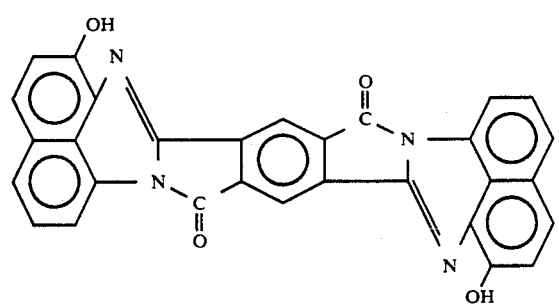
(11)
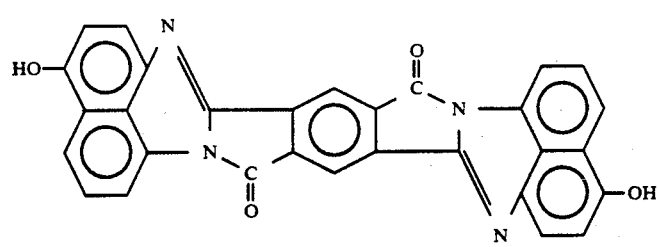
(12)
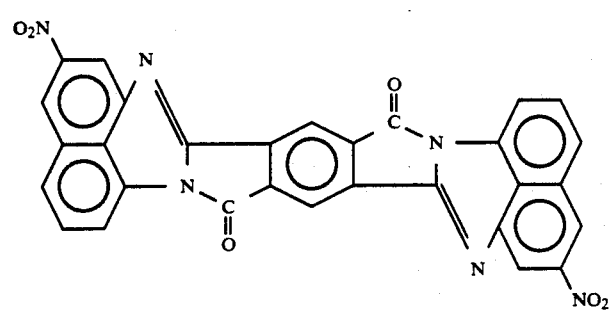
(13)

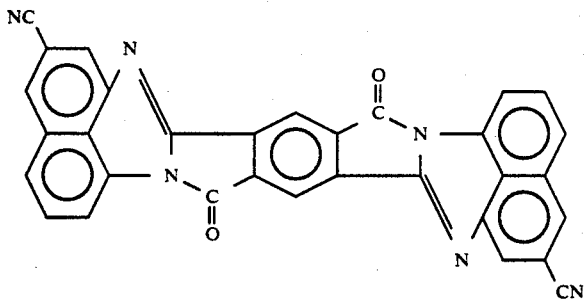
(14)
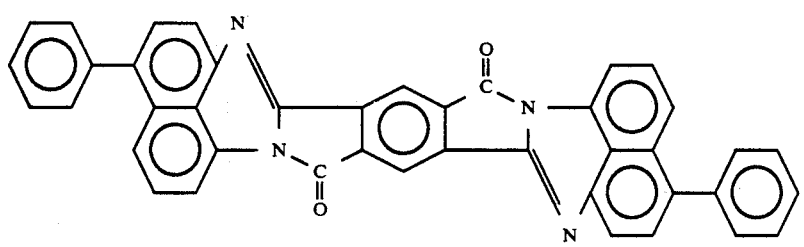
(15)
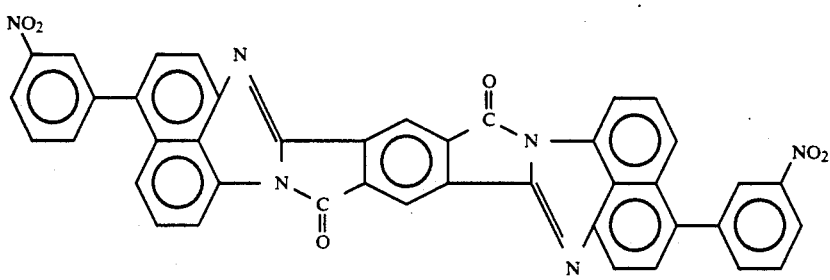
(16)
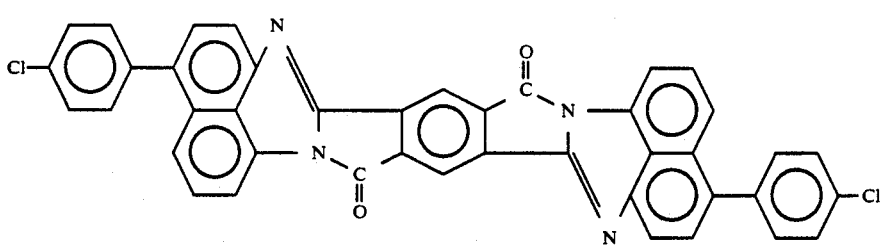
(17)
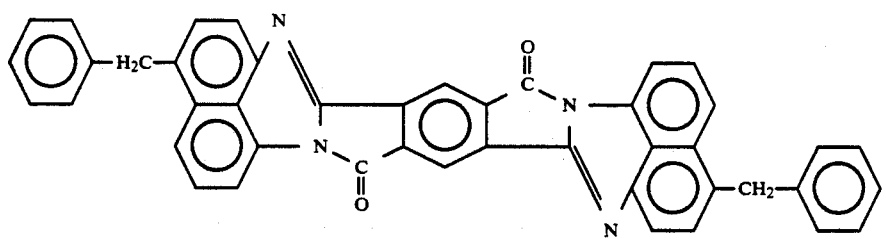
(18)
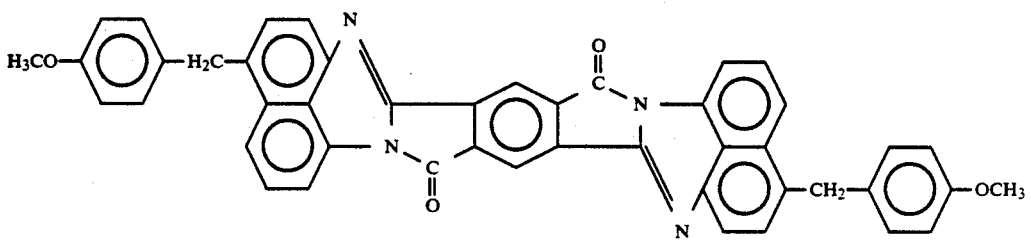
(19)

-continued
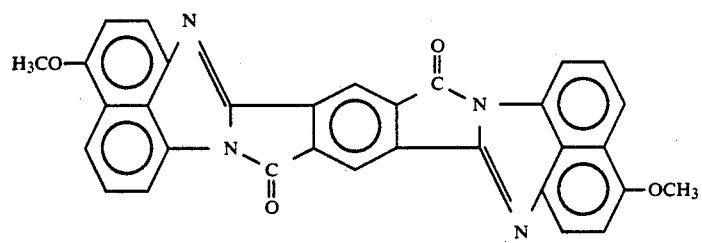
(20)
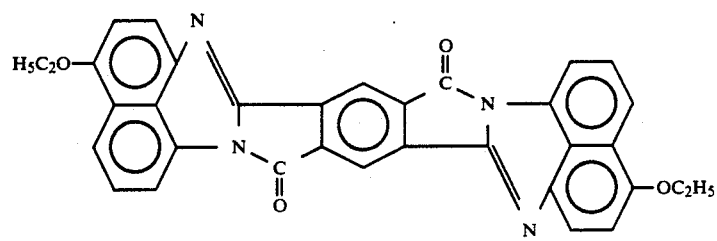
(21)
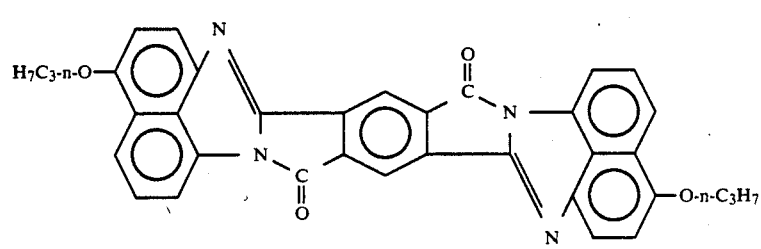
(22)
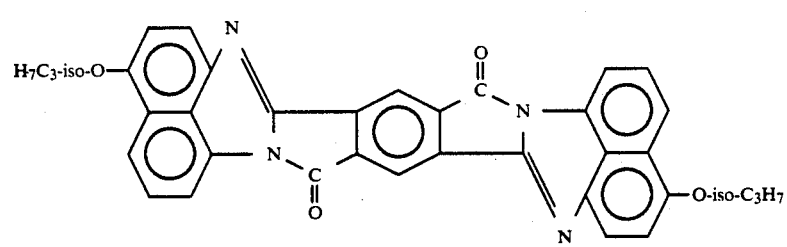
(23)
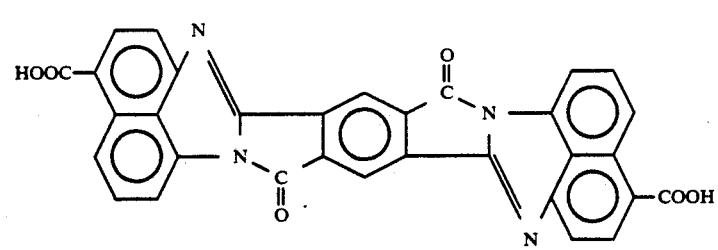
(24)
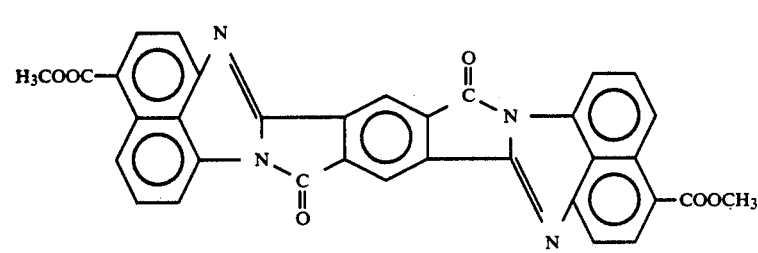
(25)

-continued
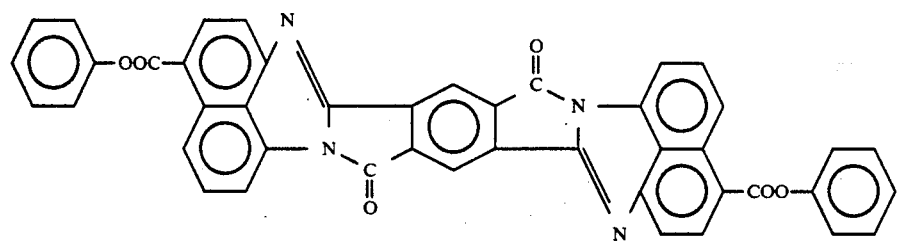
(26)
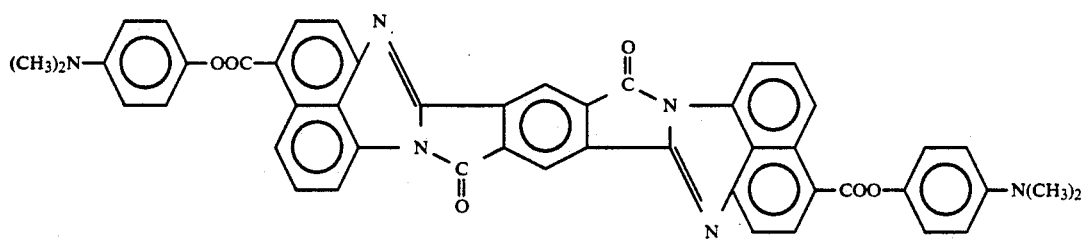
(27)
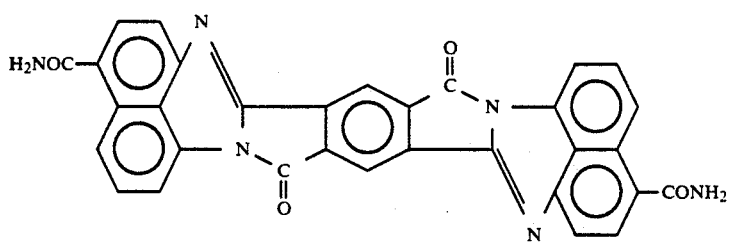
(28)
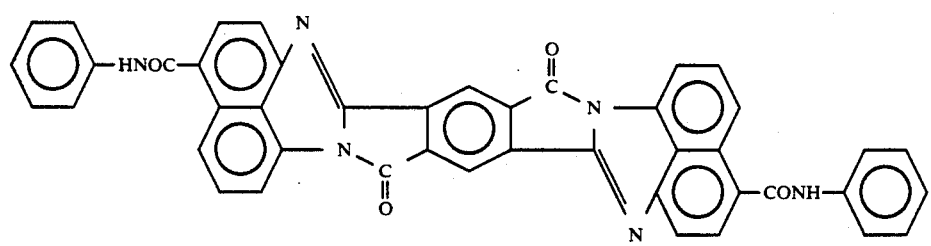
(29)
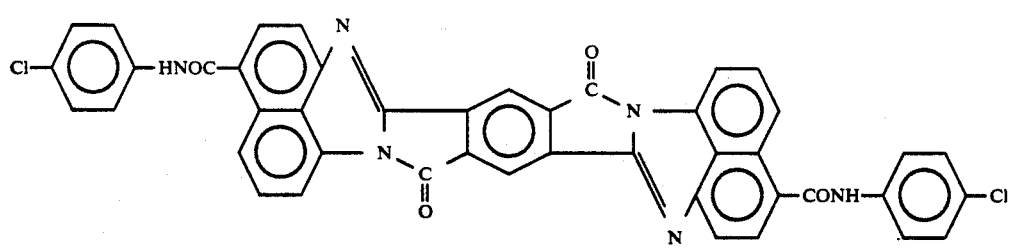
(30)
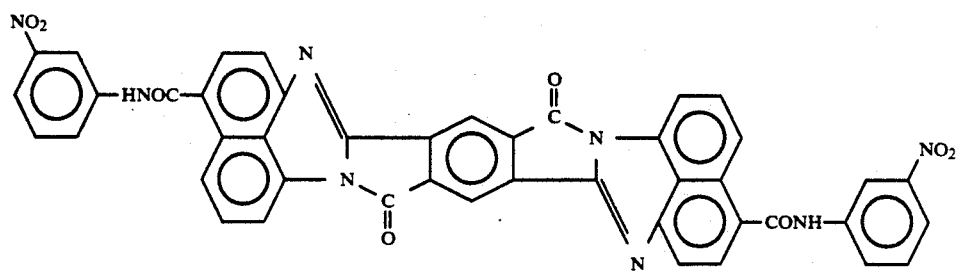
(31)

The pyrimindine compounds represented with the above formulae (I) and (II), which are novel compounds, have photoconductivity. Thus, the present invention provides novel photosensitive members, which especially have excellent properties as those for electrophotography. The members can be prepared by disposing on a conductive support one or more photosensitive layers containing either the compound of the formula (I) or the compound of the formula (II), or the mixture of the compounds of the formulae (I) and (II). Various types of the photosensitive layers can be considered.

For example, the pyrimidine compounds of the present invention may be dispersed in a polymer binder and applied on a conductive support, to make a photosensitive layer. In another process, the pyrimidine compounds of the present invention may be utilized as a charge-generating substance, since their charge-generating ability is especially superior among their photoconductive properties. That is, the pyrimidine compounds may be dispersed in a binder polymer containing a charge-transporting substance (the binder polymer is not necessarily used when the charge-transporting substance has a coating membrane-forming ability), to form a photosensitive layer. Further, it may be used to prepare the so-called multilayer type photosensitive members for electrophotography having a multilayer type photosensitive layer which comprises a laminate of a charge-generating layer containing the pyrimidine compounds and a charge-transporting layer.

Usable above-mentioned conductive supports are those substrates which per se have conductivity, such as aluminum, aluminum alloy, copper, zinc, stainless steel, nickel, chromium, titanium, etc., plastics having a conductive coating membrane layer formed by a vacuum evaporation method or the like, of aluminum, aluminum alloy, indium oxide or tin oxide, substrates comprising plastics, paper, or the like, impregnated with conductive particles or plastics having conductive polymers.

Figure 2:
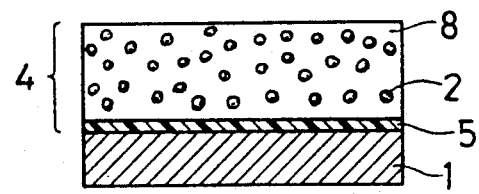
Figure 3:
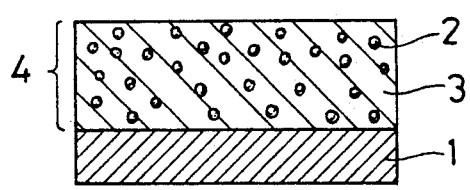
Figure 4:
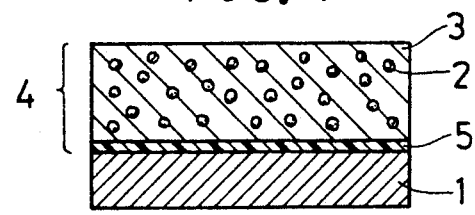
Figure 5:
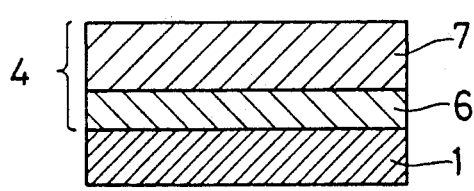

FIGS. 1-8 show each a representative form of the photosensitive members for electrophotography of the present invention. In the photosensitive members of FIG. 1 and FIG. 2, the pyrimidine compounds of the present invention act as a photoconductor, and the charge-generation and the charge-transportation are effected through the intermediation of the pyrimidine compounds. In the FIG. 2, 1 denotes a conductive support, 2 denotes the pyrimidine compound, 4 denotes a photosensitive layer, 5 denotes an undercoating layer and 8 denotes a binder. In FIG. 3 and FIG. 4 are shown those photosensitive members in which a photosensitive layer 4 comprising a dispersion of the pyrimidine compound 2 as the charge-generating substance in a charge-transporting substance-containing layer 3 is provided directly or through an undercoating layer 5 on a conductive support 1. As shown in FIG. 5-FIG. 8, a multilayer type photosensitive layer 4 comprising a laminate of a charge-generating layer 6 consisting mainly of the pyrimidine compound of the present invention, as the charge-generating substance, and a charge-transporting layer 7 consisting mainly of a charge-transporting substance, may be provided on a conductive support 1 to prepare photosensitive members. An undercoating layer 5 may be interposed between the conductive support 1 and the shown in FIG. 5 and FIG. 6 or FIG. 7 and FIG. 8, when the photosensitive layer 4 is composed of two layers, either of the charge-generating layer 6 and the charge-transporting layer 7 may be the upper layer. With a multilayer type photosensitive member having a photosensitive layer 4 composed of two layers, especially superior photosensitive members for electrophotography are obtained.

The pyrimidine compounds of the present invention constituting the photosensitive layer 4 of laminate type may form the charge-generating layer 6 on the conductive support 1 or on the charge-transporting layer 7, directly or through an intermediate layer such as the undercoating layer 5, etc. The forming of such charge-generating layer is effected by vacuum evaporation of an pyrimidine compound of the present invention as the charge-generating substance, or by application of a dispersion obtained by dispersing an pyrimidine compound of the present invention is a suitable solvent and, if necessary, mixing with a binder, or of a dispersion obtained by dispersing an pyrimidine compound of the present invention in a suitable solvent containing a binder dissolved therein. Generally speaking, the latter method is preferred.

When the charge-generating layer is prepared by application method, dispersion of the pyrimidine compound in a binder solution can be performed efficiently by using ball mill, sand mill, roll mill, attritor, vibration mill, supersonic disperser, etc., and application of the dispersion can be performed efficiently by using air doctor coater, blade coater, spray coater, hot coater, squeeze coater, etc.

As the binder used here, there can be mentioned, for example, those insulating resins, such as polycarbonate resin, acrylic resin, polyester resin, polystyrene resin, polyamide resin, polyarylate resin, phenoxy resin, a copolymer resin containing two or more of the recurring units of the foregoing resins, such as vinyl chloride/vinyl acetate copolymer resin, acrylonitrile/styrene copolymer resin, etc., and the like. However, the binder is not limited to these insulating resins, but any of generally used resins can be used solely or as a mixture of two or more of them.

Further, as the solvent for dissolving the binder used, can be used, for example, alcohols such as methanol, ethanol, isopropanol, etc., ketones such as acetone, methyl ethyl ketone, cyclohexanone, etc., esters such as ethyl acetate, butyl acetate, etc., ethers such as tetrahydrofuran, dioxane, etc., aromatic hydrocarbons such as benzene, toluene, xylene, etc., aprotic polar solvents such as N,N-dimethylformamide, N,N-dimethylacetamide, dimethyl sulfoxide, etc., and the like.

The membrane thickness of the charge-generating layer 6 thus formed is suitably 0.01-20 $\mu$m, preferably 0.05-5 $\mu$m, more preferably 0.1-2 $\mu$m. Further, it is necessary to granulate the imidazole compound 2 of the present invention into fine particles having a particle size of 5 $\mu$m or less, preferably 3 $\mu$m or less, most preferably 1 $\mu$m or less. The binder resin contained in the charge-generating layer is suitably 80% by weight or less, preferably 40% by weight or less.

The charge-transporting layer 7 is electrically connected with the charge-generating layer 6 and has a function of transporting the charge carriers poured in from the charge generating layer, in the presence of electric field. As materials for such charge-transporting layer, though the materials are generally classified into electron-transporting substances and hole-transporting substances, both of the two, and also a mixture of the two, can be used for the photosensitive layer of the present invention. As the electron-transporting substances, those substances having electron attractive groups such as nitro group, cyano group, etc., for example, nitrated fluorenones such as 2,4,7-trinitro-9-fluorenone, 2,4,5,7-tetranitro-9-fluorenone, etc., trinitrotoluene, and the like, are mentioned. As the hole-transporting substances, electron such as carbazole, oxazole, thiazole, oxadiazole, imidazole, pyrazoline, etc., low molecular charge-transporting substances such as aniline derivatives, arylamine derivatives, hdyrozone derivatives, stilbene derivatives, etc., high molecular charge-transporting substances such as poly-N-vinylcarbazole, hologenated poly-N-vinylcarbazole, polyvinyl pyrene, polyvinyl anthracene, etc., and the like, may used. However, the charge-transporting substances applicable to the present invention are not limited to those mentioned above. The charge-transporting substances can be used individually or as a mixture of two or more of them.

When a low molecular charge-transporting substance is used, the coating membrane can be formed by selecting a suitable binder. However, a high molecular charge-transporting substance having membrane-forming property may also be used. Further, it is also possible to mix the above-mentioned high molecular charge-transporting substance with the binder.

As the binder used here, the above-mentioned various resins used for the preparation of charge-generating layers can be used, and various solvents as described above are appliable as the solvent for binder.

The membrane thickness of the charge-generating layer thus formed is 2-100 $\mu$m, preferably 5-30 $\mu$m.

As the undercoating layer 5, high molecular organic substances such as gelatin, casein, polyvinyl alcohol, ethyl cellulose, etc., aluminum oxide, and the like, may be used, besides the high molecular polymers used as the above-mentioned binder resin.

The photosensitive layer of photosensitive members for electrophotography of the present invention may further contain one or two or more of electron accepting substances and coloring matters, for the purpose of improving sensibility, suppressing the elevation of residual electric potential and the fatigue, which appear on the repeated use, and the like.

As the electron accepting substances used here, there can be mentioned, for example, acid anhydrides such as succinic anhydride, maleic anhydride, phthalic anhydride, 4-chloronaphthalic anhydride, etc., cyano compounds such as tetracyanoethylene, terephthalmalononitrile, etc., aldehydes such as 4-nitrobenzaldehyde, etc., anthraquinones such as anthraquinoe, 1-nitroanthraquinone, etc., polycyclic or heterocyclic nitro compounds such as 2,4,7-trinitrofluorenone, 2,4,5,7-tetranitrofluorenone, etc., and the like. They are used as chemical sensitizers.

As the coloring matters, those organic photoconductive compounds such as xanthene dyes, thiazine dyes, triphenylmethane dyes, quinoline pigments, copper phthalocyanine pigments, etc., are mentioned. They may be used as a kind of optical sensitizers.

Further, the photosensitive layer of the photosensitive members for electrophotography of the present invention may contain known plasticizers, for the purpose of improving molding characteristics, flexibility and mechanical strength. As the plasticizer, there can be mentioned dibasic acid esters, fatty acid esters, phosphoric acid esters, phthalic acid esters, chlorinated paraffins, epoxy-type plasticizers, and the like. The photosensitive layer may contain, if necessary, anti-oxidants, ultraviolet ray absorbing agents, and the like.

The invention is more concretely explained in the following, by giving examples. However, the invention shall never be limited to those Examples.

EXAMPLES 1

In 200 ml of nitrobenzene, 0,474 g (3.0 m mol) of 1,8-diaminonaphthalene was treated with 0.327 g (1.5 m mol) of pyromellitic anhydride at 200° C. for 24 hours while stirring. As the reaction proceeded, formation of precipitates was observed. Then, the precipitates were collected by filtration and washed 3 times with 500 ml each of tetrahydrofuran, 3 times with 500 ml each of nitrobenzene, 3 times with 500 ml each of diethyl ether, and further 5 times with 2 l of acetone. The crystals thus obtained were dried at 60° C. under vacuum, whereby 0.56 g of a colored compound was obtained (yield: 70%):

The properties of the compound are as follows.
Melting point: above 300° C.
Elementary analysis ($C_{30}H_{14}O_2N_4$)

|       | Calculated | Found |
|-------|------------|-------|
| C (%) | 77.9       | 77.6  |
| H (%) | 3.0        | 3.2   |
| N (%) | 12.1       | 11.7  |

Figure 9:
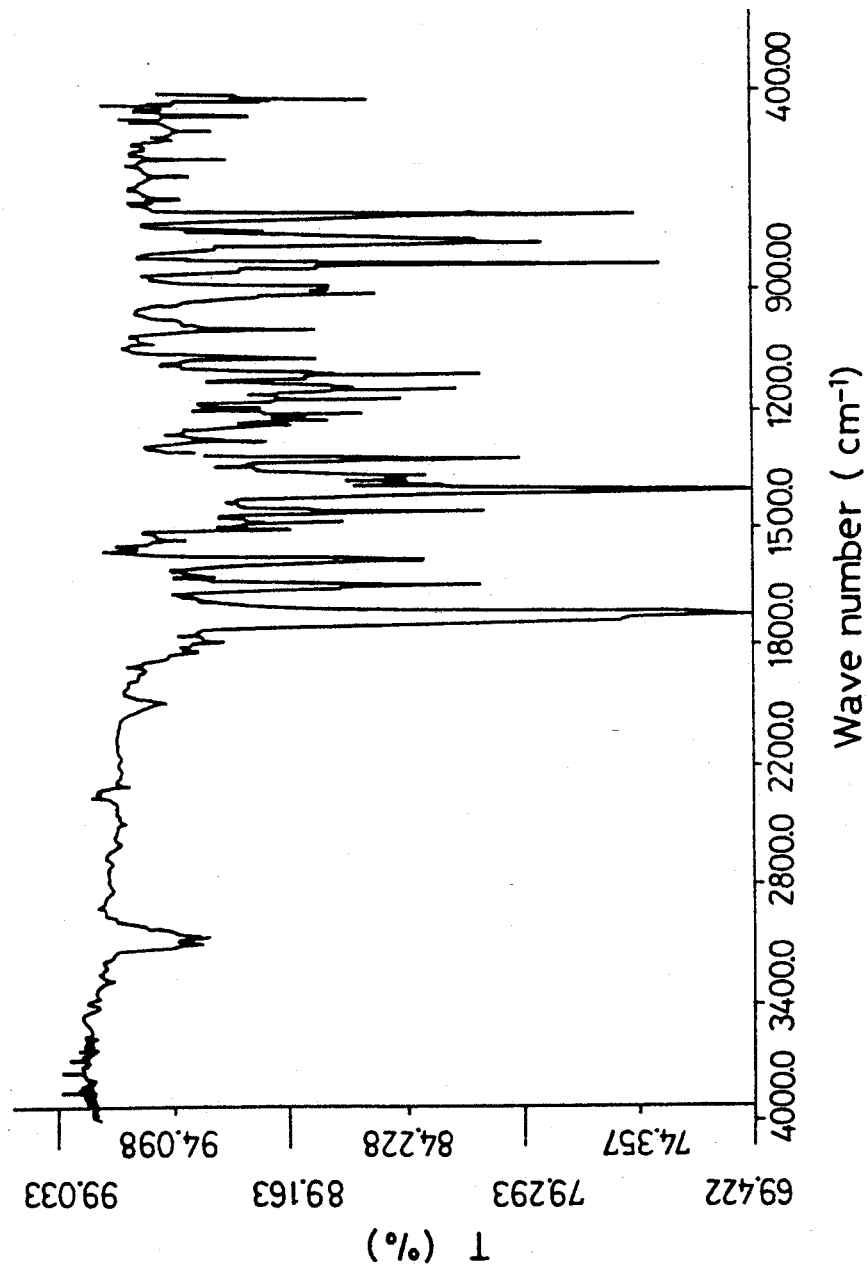
FIGS. 9 and 10 are an IR absorption spectrum and a visual region absorption spectrum of a representative pyrimidine compound (1,2,4,5-Benzoylenebis(naphtho[1,8-de]pyrimidine)compound) according to the invention, respectively.

IR absorption spectrum is shown in the IR chart of FIG. 9 obtained with an infrared absorption spectroscopy.

Figure 10:
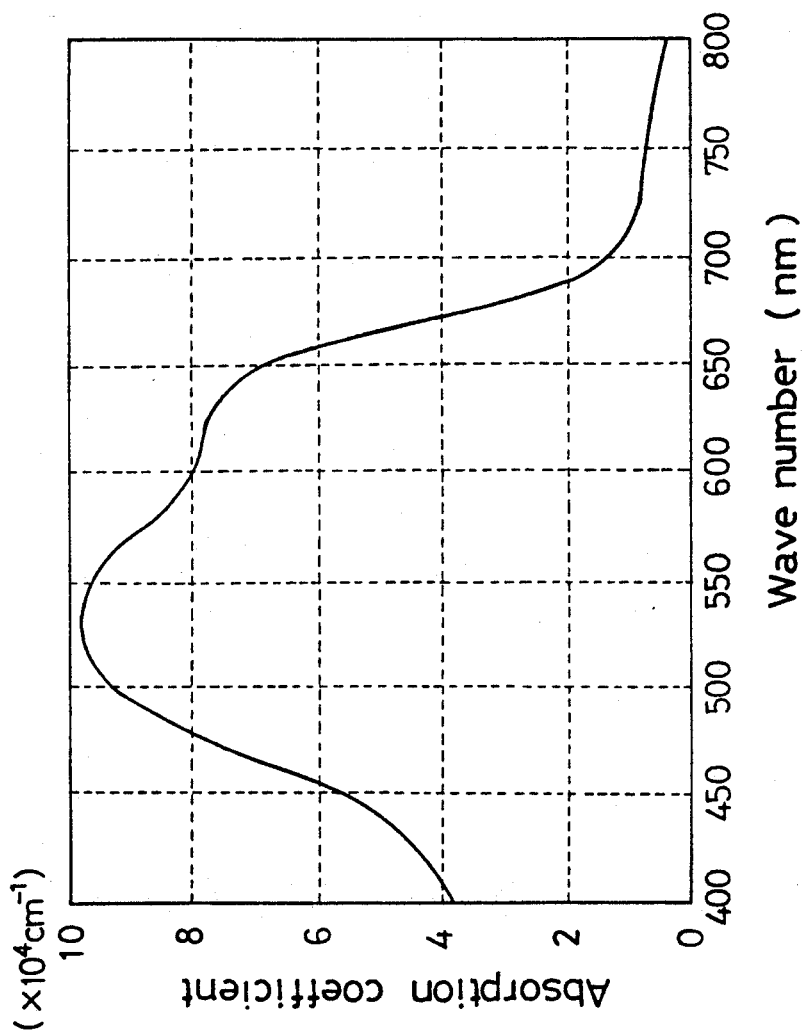

Visual region absorption spectrum is shown in the chart of FIG. 10 obtained by a visible light absorption spectroscopy using as a sample thin phenoxy resin film containing the compound dispersed.

From the above results, the compound was determined to be a mixture of pyrimidine compounds of the following formalae (1) and (2).

The compound is novel pyrimidine compound.

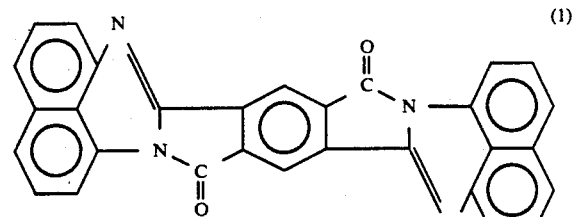

EXAMPLE 2

A dispersion obtained by dispersing 2 parts by weight of the pyrimidine compound No. 2, which was prepared from pyrometallic anhydride and 1,8-diamino-7-methyl naphthalene in the same manner as Example 1 and 1 part by weight of a phenoxy resin (PKHH, from Union Carbide Corp.) in 8 parts by weight of dioxane for 12 hours by means of a ball mill disperser, was applied onto the surface of a PET coated with aluminum by vacuum evaporation (polyethylene terephthalate: Metalumy #100 from Toray Industries, Inc.) by means of a Baker applicator and dried at 80° C. for 1 hour, whereby a photosensitive member of the form shown in FIG. 1 having a photosensitive layer of 10 μm thick was prepared.

The photosensitive member thus prepared was corona electrified by means of an electrostatic paper analyzer, Model SP-428 from Kawaguchi Electric Co., Ltd. at +5 KV in static mode and, after maintaining in dark place for lux, to investigate its electrification characteristics. As the electrification characteristics, initial electric potential ($V_0$), exposure amount necessary for attenuating the potential as attenuated in darkness for 5 seconds the half ($E1\kappa$), residual potential at 5 seconds after the start of exposure ($V_R$) and charge retention coefficient as attenuated in darkness for 5 seconds ($V_K$) were measured. The results obtained are shown in Table 1, together with the results of the following Example 3-5.

EXAMPLES 3-5

The above described pyrimidine compounds No. 12,15,18 each were synthesized in the same manner as Example 1 except for using 1,8-diamino-5-hydroxynaphthalene(Example 3), 1,8-diamino-5-phenylnaphthalene(Example 4), 1,8-diamino-5 -benzylnaphthalene(Example 5), respectively, instead of 1,8-diaminonaphthalene.

Photosensitive members having the form shown in FIG. 2 were prepared in the same manner as Example 2, except that each of the pyrimidine compounds obtained above was used instead of the pyrimidine compound No. 2 and, as the substrate, was used one prepared by forming an undercoating layer of vinyl chloride/vinyl acetate/maleic anhydride copolymer (Ethulek MF-10, from Sekisui Chemical Co., Ltd.) having a thickness of 0.05 μm on the PET coated with aluminum by vacuum evaporation which was used in Example 2. With these photosensitive members, the same measurements as Example 2 were effected. The result obtained are shown in Table 1.

TABLE 1

Results of measurements by means of the electrostatic paper analyzer

| Example | Pyrimidine compound No. | $V_0$ (V) | $E_{\frac{1}{2}}$ (lux · sec) | $V_R$ (V) | $V_K$ (%) |
|---|---|---|---|---|---|
| 2 | 2 | +376 | 12.0 | +8 | 94 |
| 3 | 12 | +333 | 14.0 | +11 | 91 |
| 4 | 15 | +385 | 11.0 | +12 | 95 |
| 5 | 18 | +401 | 13.0 | +15 | 98 |

EXAMPLE 6

A dispersion obtained by dispersing 2 parts by weight of the pyrimidine compound No. 3, which was prepared in the same manner as Example 1, except for using 1,8-diamino-5-methylnaphthalene instead of 1,8-diamino-naphthalene, 15 parts by weight of 2,4,7-trinitro-9-fluorenone and 15 parts by weight of a polycarbonate resin (Iupiron, from Mitsubishi Gas Chemical Company Inc.) in 188 parts by weight of dichloromethane for 12 hours by means of a ball mill disperser, was applied onto the surface of the PET coated with aluminum by vacuum evaporation (the same one as used in Example 2) by means of a Baker applicator and of the form shown in FIG. 3 having a photosensitive layer of 20 μm thick was prepared. Then, the same measurements as Example 2 were effected, except that the corona electrification was performed at −5 KV, instead of +5 KV in Example 2, in the electrostatic copying test of the phototsensitive member. The results obtained are shown in Table 2, together with the results of the following Examples 7–9.

EXAMPLES 7–9

The above described pyrimidine compounds No. 11,13,16 each were synthesized in the same manner as Example 1 except for using 1,8-diamino-7-hydroxynaphthalene (Example 7), 1,8-diamino-6-nitronaphthalene (Example 8), 1,8-diamino-5-(m-nitrophenyl)-naphthalene (Example 9), respectively, instead of 1,8-diamino-naphthalene.

Photosenstive members having the form shown in FIG. 4 prepared in the same manner as Example 6, except that each of the pyrimidine compounds obtained above was used instead of the pyrimidine compound No. 3 and, as the substrate, was used one prepared by forming an undercoating layer of a vinyl chloride/vinyl acetate/maleic anhydride copolymer having a thickness of 0.05 μm on the PET coated Example 6. With these photosensitive members, the same measurements as Example 6 were effected. The results obtained are shown in Table 2.

TABLE 2

Results of measurements by means of the electrostatic paper analyzer

| Example | Pyrimidine compound No. | $V_0$ (V) | $E_{\frac{1}{2}}$ (lux · sec) | $V_R$ (V) | $V_K$ (%) |
|---|---|---|---|---|---|
| 6 | 3 | −412 | 15.0 | −15 | 88 |

TABLE 2-continued

Results of measurements by means of the electrostatic paper analyzer

| Example | Pyrimidine compound No. | $V_0$ (V) | $E_{\frac{1}{2}}$ (lux · sec) | $V_R$ (V) | $V_K$ (%) |
|---|---|---|---|---|---|
| 7 | 11 | −399 | 12.0 | −20 | 89 |
| 8 | 13 | −387 | 11.0 | −17 | 81 |
| 9 | 16 | −376 | 9.0 | −14 | 80 |

EXAMPLE 10

A dispersion obtained by dispersing 2 parts by weight of the pyrimidine compound No. 1 prepared in Example 1 and 1 part by weight of a phenoxy resin (the same one as used in Example 2) in 97 parts by weight of 1,4-dioxane for 12 hours by means of a ball mill disperser, was applied onto the same PET coated with aluminum by vacuum evaporation as used in Example 2 by means of a Baker applicator and dried at room temperature for 1 hour, whereby a charge-generating layer of 0.5 μm thick was formed.

Next, 1 part by weight of a hydrazone series compound represented by the following formula,

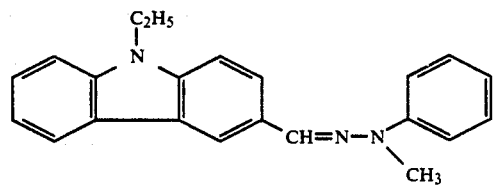

1 part by weight of a polycarbonate resin (the same one as used in Example 6) and 8 parts by weight of dichloromethane were mixed together and dissolved by stirring with a stirrer. The solution thus obtained was applied onto the charge-generating layer by means of a Baker applicator and then dried at 80° C. for 1 hour, whereby photosensitive member of the form shown in FIG. 5 having a photosensitive layer of 20 μm thick was prepared. The same measurements as Example 6 were effected with regard to this photosensitive member. The results obtained are shown in Table 3, together with the results of the following Examples 11–13.

EXAMPLES 11–13

The above described pyrimidine compounds No. 10,17,18 each were synthesized in the same manner as Example 1 except for using 1,8-diamino-5-bromonaphthalene (Example 11), 1,8-diamino-5-(p-chlorophenyl)-naphthalene (Example 12), 1,8-diamino-5-benzylnaphthalene (Example 13), respectively, instead of 1,8-diaminonaphalene.

Figure 6:
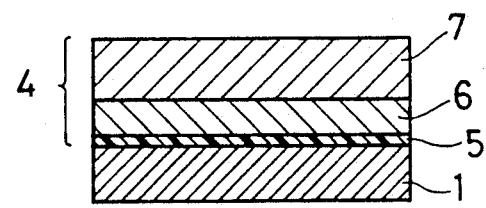

Photosensitive members having the form shown in FIG. 6 were prepared in the same manner as Example 10, except that each of the pyrimidine compounds obtained above was used instead of the pyrimidine compound No. 1 and, as the substrate, was used one prepared by forming an undercoating layer of a vinyl chloride/vinyl acetate/maleic anhydride copolymer (the same one as used in Example 10) having a thickness of 0.05 μm on the PET coated with aluminum by vacuum evaporation which was used in Example 10. With regard to these photosensitive members, the same measurements as Example 10 were effected. The results obtained are shown in Table 3.

TABLE 3

| Example | Pyrimidine compound No. | Results of measurements by means of the electrostatic paper analyzer | | | |
|---|---|---|---|---|---|
| | | $V_0$ (V) | $E_{\frac{1}{2}}$ (lux · sec) | $V_R$ (V) | $V_K$ (%) |
| 10 | 1 | −721 | 4.0 | −7 | 96 |
| 11 | 10 | −700 | 5.0 | −9 | 95 |
| 12 | 17 | −699 | 7.0 | −12 | 90 |
| 13 | 18 | −721 | 9.0 | −17 | 97 |

EXAMPLE 14

One part by weight of a hydrazone series compound represented by the following formula

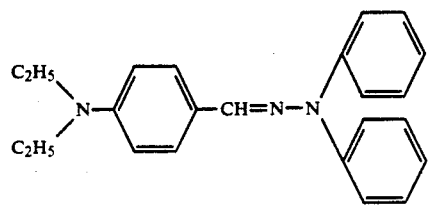

1 part by weight of a polycarbonate resin (the same one as used in Example 6) and 8 parts by weight of dichloromethane were mixed together and dissolved by stirring with a stirrer. The solution thus obtained was applied onto the PET coated with aluminum by vacuum evaporation (the same one as used in Example 2), by means of a Baker applicator, and dried at 80° C. for 1 hour, whereby a charge-transporting layer having a membrane thickness of 19.5 μm was formed.

Figure 7:
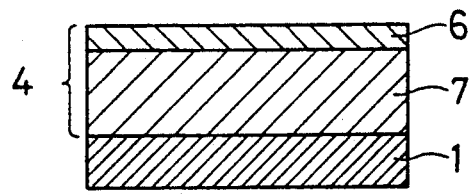

Next, a dispersion obtained by dispersing 2 parts by the same manner as Example 1) and 1 part by weight of a phenoxy resin (the same one as used in Example 2) in 97 parts by weight of 1,4-dioxane for 12 hours by means of a ball mill disperser, was applied onto the charge-transporting layer by means of a Baker applicator, and then a photosensitive member of the form shown in FIG. 7 having a photosensitive layer of 20 μm thick was prepared. With regard to this photosensitive member, the same measurements as Example 2 were effected. The results obtained are shown in Table 4, together with the results of the following Examples 15-17.

EXAMPLES 15-17

Figure 8:
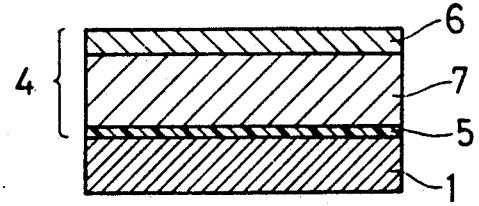

The above described pyrimidine compounds No. 6,8,14 each were synthesized in the same manner as Example 1 except for using 1,8-diamino-5-ethylnaphthalene (Example 15), 1,8-diamino-5-chloronaphthalene (Example 16), 1,8-diamino-5-cyanonaphthalene (Example 17), respectively, instead of Photosensitive members having the form shown in FIG. 8 were prepared in the same manner as Example 14, except that each of the pyrimidine compounds obtained above was used instead of the pyrimidine compound No. 5 and, as the substrate, was used one prepared by forming an undercoating layer of a vinyl chloride/vinyl acetate/maleic anhydride copolymer (the same one as used in Example 14) having a thickness of 0.05 μm on the PET coated with aluminum by vacuum evaporation which was used in Example 14. With regard to these photosensitive members, the same measurements as Example 14 were effected. The results obtained are shown in Table 4.

TABLE 4

| Example | Pyrimidine compound No. | Results of measurements by means of the electrostatic paper analyzer | | | |
|---|---|---|---|---|---|
| | | $V_0$ (V) | $E_{\frac{1}{2}}$ (lux · sec) | $V_R$ (V) | $V_K$ (%) |
| 14 | 5 | +698 | 9.0 | +11 | 89 |
| 15 | 6 | +678 | 9.0 | +9 | 81 |
| 16 | 8 | +700 | 7.0 | +17 | 86 |
| 17 | 14 | +704 | 8.0 | +16 | 89 |

Comparative Example 1

A photosensitive member was prepared according to the same manner as Example 2, except that a polycyclic quinone series pigment (Monolite Red 2Y, from I.C.I. Ltd.) of the formula

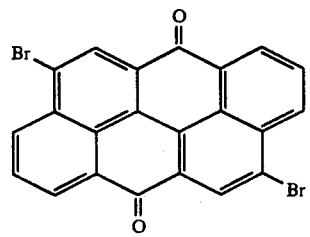

was used instead of the pyrimidine compound No. 2. Then, the same measurements as example 2 were effected with regard to the photosensitive member. The results obtained are shown in Table 5.

Comparative Example 2

A photosensitive member was prepared according to series pigment (Cinquasia Red Y RT-759-D, from Ciba-Geigy Ltd.) of the formula

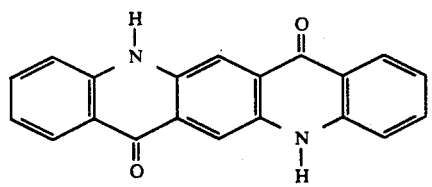

was used instead of the pyrimidine compound No. 12. The same measurements as Example 3 were effected with regard to the photosensitive member. The results obtained are shown in Table 5.

Comparative Example 3

A photosensitive member was prepared according to the same manner as Example 6, except that an isoindolinone series pigment (Irgazin Yellow 2RLT, from Ciba-Geigy Ltd.) of the formula

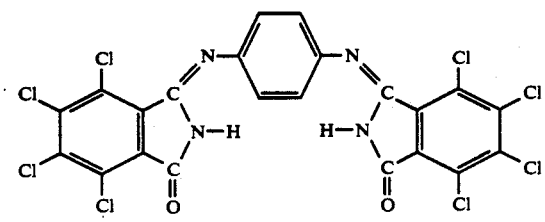

was used instead of the pyrimidine compound No. 3. The same measurements as Example 6 were effected with regard to the photosensitive member. The results obtained are shown in Table 5.

Comparative Example 4

A photosensitive member was prepared according to the same manner as Example 7, except that an indigo series pigment (Vat Blue 1, from Mitsui Toatsu Dyestuff Inc.) of the formula

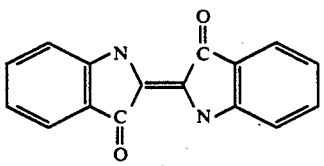

was used instead of the pyrimidine compound No. 11. The same measurements as example 7 were effected with regard to the photosensitive member. The results obtained are shown in Table 5.

Comparative Example 5

A photosensitive member was prepared according to the same manner as Example 10, except that a thioindigo series pigment (Vat Red 41, from Mitsui Toatsu Dyestuff Inc.) of the formula

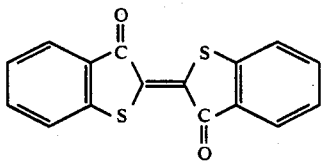

was used instead of the pyrimidine compound No. 1. The same measurements as Example 10 were effected with regard to the photosensitive member. The results obtained are shown in Table 5.

Comparative Example 6

A photosensitive member was prepared according to the same manner as Example 12, except that a xanthene series dyestuff (Eosine Y) of the formula

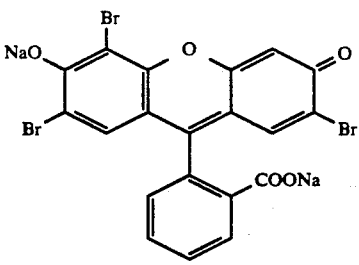

was used instead of the pyrimidine compound No. 17. The same measurements as Example 12 were effected with regard to the photosensitive member. The results obtained are shown in Table 5.

Comparative Example 7

A photosensitive member was prepared according to the same manner as Example 14, except that an acridine series dyestuff (Acridine Yellow, from Chroma Ltd.) of the formula

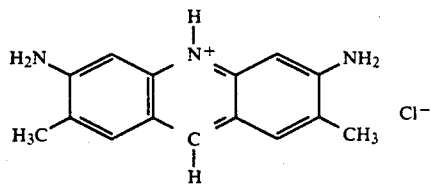

was used instead of the pyrimidine compound No. 5. The same measurements as Example 14 were effected with regard to the photosensitive member. The results obtained are shown in Table 5.

Comparative Example 8

A photosensitive member was prepared according to the same manner as Example 17, except that a triphenylmethane series dyestuff (Ethylviolet) of the formula

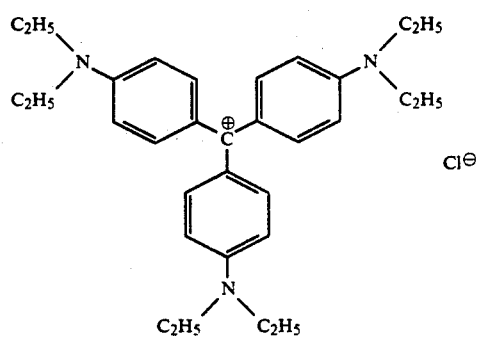

was used instead of the pyrimidine compound No. 14. The same measurements as Example 17 were effected with regard to the photosensitive member. The results obtained are shown in Table 5.

TABLE 5

| Comparative Example | Results of measurements by means of the electrostatic paper analyzer | | | |
|---|---|---|---|---|
| | $V_0$ (V) | $E\frac{1}{2}$ (lux · sec) | $V_R$ (V) | $V_K$ (%) |
| 1 | +200 | 54 | +45 | 80 |
| 2 | +300 | 39 | +55 | 75 |
| 3 | −365 | 89 | −50 | 70 |
| 4 | −390 | 32 | −60 | 75 |
| 5 | −400 | 40 | −30 | 80 |
| 6 | −405 | 33 | −35 | 81 |
| 7 | +355 | 45 | +40 | 76 |
| 8 | +370 | 42 | +45 | 77 |

What is claimed is:

1. A photosensitive member comprising a photosensitive layer containing the compound of the following formula (I) or (II) on a conductive support:

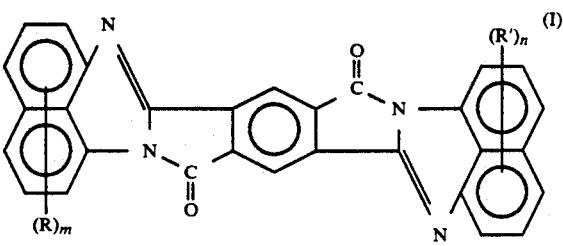

-continued

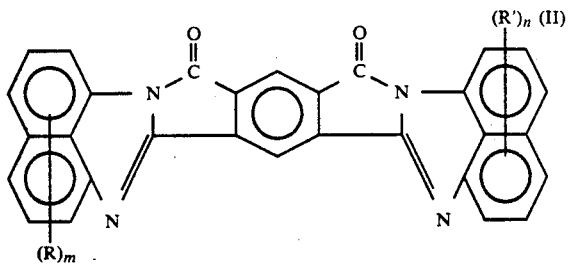

wherein R and R' are the same or different and are each selected from the group consisting of a hydrogen atom; halogen atom; hydroxyl group; nitro group; cyano group; an alkyl group; an alkyl substituted with at least one of a halogen atom, hydroxy group, nitro group or cyano group; an alkoxyl group; an alkoxyl group substituted with at least one of a halogen atom, hydroxy group, nitro group or cyano group; an aryl group; an aryl group substituted with at least one of a halogen atom, nitro group, cyano group, hydroxy group, lower alkyl group, lower alkoxy group or di-lower alkylamino group; an aralkyl group; an aralkyl group substituted with at least one of a halogen atom, nitro group, cyano group, hydroxy group, lower alkyl group, lower alkoxy group or di-lower alkylamino group; a carboxyl group; a carboxylate group; a carbamoyl group; and a carbamoyl group substituted with at least a halogen atom, nitro group or cyano group; and m and n each are an integer from 1 to 6, wherein the photosensitive layer is a multilayer type, consisting of a charge-generating layer and a charge-transporting layer, the former containing the compound of formula (I) or (II).

2. The photosensitive member of claim 1, wherein the charge-generating layer is formed to 0.01-20 μm in thickness.

3. The photosensitive member of claim 1, wherein the charge-transporting layer is formed to 2-100 μm in thickness.

4. The photosensitive member of claim 1, wherein R and R' are each a hydrogen atom.

5. The photosensitive member of claim 1, wherein R and R' are each a halogen atom.

6. The photosensitive member of claim 1, wherein the halogen atom is chlorine or bromine atom.

7. The photosensitive member of claim 1, wherein R and R' are each a hydroxyl group.

8. The photosensitive member of claim 1, wherein R and R' are each a nitro group.

9. The photosensitive member of claim 1, wherein R and R' are each a cyano group.

10. The photosensitive member of claim 1, wherein the alkyl group which may be substituted is a methyl or ethyl group.

11. The photosensitive member of claim 1, wherein the alkoxyl group is methoxy, ethoxy or propoxy group.

12. The photosensitive member of claim 1, wherein the aryl group which may be substituted is a phenyl group which may be substituted by a halogen atom, a lower alkyl group, a lower alkoxyl group, a nitro group or a cyano group.

13. The photosensitive member of claim 1, wherein the aralkyl group which may be substituted is a benzyl group which may be substituted by a lower alkoxyl group.

* * * * *